United States Patent
Lesho

(10) Patent No.: US 7,553,280 B2
(45) Date of Patent: *Jun. 30, 2009

(54) IMPLANTED SENSOR PROCESSING SYSTEM AND METHOD

(75) Inventor: Jeffery C. Lesho, Brookeville, MD (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/332,619

(22) PCT Filed: Jun. 27, 2001

(86) PCT No.: PCT/US01/20390

§ 371 (c)(1),
(2), (4) Date: Oct. 21, 2003

(87) PCT Pub. No.: WO02/02005

PCT Pub. Date: Jan. 10, 2002

(65) Prior Publication Data

US 2004/0054385 A1    Mar. 18, 2004

Related U.S. Application Data

(63) Continuation-in-part of application No. 09/605,706, filed on Jun. 29, 2000, now Pat. No. 6,400,974.

(51) Int. Cl.
*A61B 5/00* (2006.01)
*A61B 6/00* (2006.01)

(52) U.S. Cl. .................. 600/365; 600/309; 600/310; 600/316; 600/476; 600/477

(58) Field of Classification Search ............ 600/316, 600/317, 310, 322, 341–343, 473, 476, 345, 600/347, 302, 365
See application file for complete search history.

(56) References Cited

U.S. PATENT DOCUMENTS 3,229,684 A    1/1966  Nagumo et al.

(Continued)

FOREIGN PATENT DOCUMENTS

GB    2 235 496 A    9/1999

(Continued)

OTHER PUBLICATIONS

Huang, Q., et al., "A 0.5-mW Passive Telemetry IC for Biomedical Applications", IEEE Journal of Solid State Circuits, vol. 33, No. 7, Jul. 1998, pp. 937-945.

(Continued)

*Primary Examiner*—Robert L Nasser
*Assistant Examiner*—Navin Natnithithadha
(74) *Attorney, Agent, or Firm*—Rothwell, Figg, Ernst & Manbeck

(57) ABSTRACT

A quantitative measurement system includes an external unit (101a) and an internal unit (102a) are provided for obtaining quantitative analyte measurements, such as within the body. In one example of an application of the system, the internal unit (102a) would be implanted either subcutaneously or otherwise within the body of a subject. The internal unit (102a) contains optoelectronics circuitry (102b), a component of which may be comprised of a fluorescence sensing device. The optoelectronics circuitry (102b) obtains quantitative measurement information and modifies a load (102c) as a function of the obtained information. The load (102c) in turn varies the amount of current through coil (102d), which is coupled to a coil (101f) of the external unit (101a). A demodulator (101b) detects the current variations induced in the external coil (101f) by the internal coil (102d) coupled thereto, and applies the detected signal to processing circuitry, such as a pulse counter (101c) and computer interface (101d), for processing the signal into computer-readable format for inputting to a computer (101e).

12 Claims, 10 Drawing Sheets

U.S. PATENT DOCUMENTS

| | | | |
|---|---|---|---|
| 3,576,554 A | 4/1971 | Temps, Jr. et al. | |
| 3,800,300 A | 3/1974 | Van Oosterhout | |
| 3,853,117 A | 12/1974 | Murr | |
| 3,872,455 A | 3/1975 | Fuller et al. | |
| 3,949,388 A * | 4/1976 | Fuller | 128/903 |
| 3,972,320 A | 8/1976 | Kalman | |
| 4,041,954 A | 8/1977 | Ohara | |
| 4,160,971 A | 7/1979 | Jones et al. | |
| 4,186,749 A | 2/1980 | Fryer | |
| 4,361,153 A * | 11/1982 | Slocum et al. | 128/903 |
| 4,494,545 A * | 1/1985 | Slocum et al. | 128/903 |
| 5,001,054 A | 3/1991 | Wagner | |
| 5,024,224 A * | 6/1991 | Engebretson | 128/898 |
| 5,117,825 A | 6/1992 | Grevious | |
| 5,218,207 A | 6/1993 | Rosenthal | |
| 5,244,810 A | 9/1993 | Gottlieb | |
| 5,314,457 A | 5/1994 | Jeutter et al. | |
| 5,341,805 A | 8/1994 | Stavridi et al. | |
| 5,372,133 A | 12/1994 | Hogen Esch | |
| 5,517,313 A * | 5/1996 | Colvin, Jr. | 356/417 |
| 5,571,148 A * | 11/1996 | Loeb et al. | 607/56 X |
| 5,584,870 A | 12/1996 | Single et al. | |
| 5,628,310 A | 5/1997 | Rao et al. | |
| 5,630,836 A | 5/1997 | Prem et al. | |
| 5,682,149 A | 10/1997 | Hofman | |
| 5,704,352 A | 1/1998 | Tremblay et al. | |
| 5,735,887 A | 4/1998 | Barreras, Sr. et al. | |
| 5,963,132 A | 10/1999 | Yoakum | |
| 5,966,404 A | 10/1999 | Yokota et al. | |
| 5,967,986 A * | 10/1999 | Cimochowski et al. | 600/454 |
| 5,995,860 A | 11/1999 | Sun et al. | |
| 6,002,954 A * | 12/1999 | Van Antwerp et al. | 600/317 |
| 6,009,878 A | 1/2000 | Weijand et al. | |
| 6,040,194 A | 3/2000 | Chick et al. | |
| 6,049,727 A * | 4/2000 | Crothall | 600/310 |
| 6,073,050 A | 6/2000 | Griffith | |
| 6,088,608 A * | 7/2000 | Schulman et al. | 600/345 |
| 6,092,530 A | 7/2000 | Weissman et al. | |
| 6,099,482 A | 8/2000 | Brune et al. | |
| 6,141,591 A | 10/2000 | Lenarz et al. | |
| 6,144,869 A * | 11/2000 | Berner et al. | 600/347 |
| 6,175,752 B1 * | 1/2001 | Say et al. | 600/345 |
| 6,198,950 B1 | 3/2001 | Kraus | |
| 6,201,980 B1 * | 3/2001 | Darrow et al. | 600/347 |
| 6,206,835 B1 * | 3/2001 | Spillman et al. | 600/485 |
| 6,212,431 B1 | 4/2001 | Hahn et al. | |
| 6,224,550 B1 * | 5/2001 | Ellingsen | 600/366 |
| 6,231,516 B1 * | 5/2001 | Keilman et al. | 600/485 |
| 6,259,937 B1 | 7/2001 | Schulman et al. | |
| 6,268,161 B1 | 7/2001 | Han et al. | |
| 6,289,229 B1 | 9/2001 | Crowley | |
| 6,295,466 B1 * | 9/2001 | Ishikawa et al. | 600/509 |
| 6,304,766 B1 * | 10/2001 | Colvin, Jr. | 600/317 |
| 6,321,067 B1 | 11/2001 | Suga et al. | |
| 6,330,464 B1 * | 12/2001 | Colvin et al. | 600/316 |
| 6,330,885 B1 | 12/2001 | Weissman et al. | |
| 6,368,275 B1 | 4/2002 | Sliwa et al. | |
| 6,387,048 B1 | 5/2002 | Schulman et al. | |
| 6,400,974 B1 * | 6/2002 | Lesho | 600/347 |
| 6,411,108 B1 | 6/2002 | Douglas et al. | |
| 6,415,186 B1 | 7/2002 | Chim et al. | |
| 6,419,624 B1 | 7/2002 | Burton et al. | |
| 6,424,847 B1 | 7/2002 | Mastrototaro et al. | |
| 6,430,444 B1 | 8/2002 | Borza | |
| 6,443,891 B1 | 9/2002 | Grevious | |
| 6,447,448 B1 | 9/2002 | Ishikawa et al. | |
| 6,454,710 B1 | 9/2002 | Ballerstadt et al. | |
| 6,475,750 B1 | 11/2002 | Han et al. | |
| 6,505,059 B1 | 1/2003 | Kollias et al. | |
| 6,542,777 B1 | 4/2003 | Griffith et al. | |
| 6,545,483 B1 | 4/2003 | Douglas | |
| 6,546,268 B1 * | 4/2003 | Ishikawa et al. | 600/345 |
| 6,553,244 B2 * | 4/2003 | Lesho et al. | 600/347 |
| 6,564,807 B1 | 5/2003 | Schulman et al. | |
| 6,585,763 B1 | 7/2003 | Keilman et al. | |
| 6,614,406 B2 | 9/2003 | Amundson et al. | |
| 6,666,821 B2 | 12/2003 | Keimel | |
| 6,671,527 B2 | 12/2003 | Petersson et al. | |
| 6,682,490 B2 | 1/2004 | Roy et al. | |
| 6,694,158 B2 | 2/2004 | Polak | |
| 6,711,423 B2 | 3/2004 | Colvin, Jr. | |
| 6,731,961 B2 | 5/2004 | Braig et al. | |
| 6,731,976 B2 | 5/2004 | Penn et al. | |
| 6,772,011 B2 | 8/2004 | Dolgin | |
| 6,802,811 B1 | 10/2004 | Slepian | |
| 6,806,552 B2 | 10/2004 | Woo et al. | |
| 6,809,507 B2 | 10/2004 | Morgan et al. | |
| 6,809,653 B1 | 10/2004 | Mann et al. | |
| 6,809,701 B2 | 10/2004 | Amundson et al. | |
| 7,006,858 B2 * | 2/2006 | Silver et al. | 600/345 |
| 2002/0016535 A1 | 2/2002 | Martin et al. | |
| 2002/0019707 A1 | 2/2002 | Cohen et al. | |
| 2002/0032435 A1 | 3/2002 | Levin | |
| 2002/0118134 A1 | 8/2002 | Chen | |
| 2002/0123779 A1 | 9/2002 | Zarinetchi et al. | |
| 2002/0161288 A1 | 10/2002 | Shin et al. | |
| 2003/0025645 A1 | 2/2003 | Amundson et al. | |
| 2003/0050542 A1 | 3/2003 | Reihl et al. | |
| 2003/0098783 A1 | 5/2003 | Pagnol | |
| 2003/0113934 A1 | 6/2003 | Kwon | |
| 2003/0125612 A1 | 7/2003 | Fox et al. | |
| 2003/0140931 A1 | 7/2003 | Zeijlemaker et al. | |
| 2003/0169169 A1 | 9/2003 | Wuldart et al. | |
| 2003/0172940 A1 | 9/2003 | Rogers et al. | |
| 2003/0195400 A1 | 10/2003 | Glukhovsky | |
| 2003/0213495 A1 | 11/2003 | Fujita et al. | |
| 2004/0027306 A1 | 2/2004 | Amundson et al. | |
| 2004/0048394 A1 | 3/2004 | Kirchhevel | |
| 2004/0147801 A1 | 7/2004 | Kugler et al. | |
| 2004/0181155 A1 | 9/2004 | Glukhovsky | |
| 2004/0199059 A1 | 10/2004 | Brauker et al. | |

FOREIGN PATENT DOCUMENTS

| | | | |
|---|---|---|---|
| GB | 2335496 A * | 9/1999 | |
| WO | WO 97/33513 A1 | 9/1997 | |
| WO | WO 00/13003 A1 | 3/2000 | |

OTHER PUBLICATIONS

Hamici, Z., et al., "A High-Efficiency Power and Data Transmission System for Biomedical Implanted Electronic Devices", Meas. Sci. Technol., vol. 7, No. 2, 1996, pp. 192-201.

* cited by examiner

IMPLANTED SENSOR PROCESSING SYSTEM AND METHOD

BACKGROUND OF THE INVENTION

1. Field of the Invention

This invention relates to a circuit and method for processing the output of an implanted sensing device for detecting the presence or concentration of an analyte in a liquid or gaseous medium, such as, for example, the human body. More particularly, the invention relates to a circuit and method for processing the output of an implanted fluorescence sensor which indicates analyte concentration as a function of the fluorescent intensity of a fluorescent indicator. The implanted fluorescence sensor is a passive device, and contains no power source. The processing circuit powers the sensor through inductively coupled RF energy emitted by the processing circuit. The processing circuit receives information from the implanted sensor as variations as in the load on the processing circuit.

2. Background Art

U.S. Pat. No. 5,517,313, the disclosure of which is incorporated herein by reference, describes a fluorescence sensing device comprising a layered array of a fluorescent indicator molecule-containing matrix (hereafter "fluorescent matrix"), a high-pass filter and a photodetector. In this device, a light source, preferably a light-emitting diode ("LED"), is located at least partially within the indicator material, such that incident light from the light source causes the indicator molecules to fluoresce. The high-pass filter allows emitted light to reach the photodetector, while filtering out scattered incident light from the light source. An analyte is allowed to permeate the fluorescent matrix, changing the fluorescent properties of the indicator material in proportion to the amount of analyte present. The fluorescent emission is then detected and measured by the photodetector, thus providing a measure of the amount or concentration of analyte present within the environment of interest.

One advantageous application of a sensor device of the type disclosed in the '313 patent is to implant the device in the body, either subcutaneously or intravenously or otherwise, to allow instantaneous measurements of analytes to be taken at any desired time. For example, it is desirable to measure the concentration of oxygen in the blood of patients under anesthesia, or of glucose in the blood of diabetic patients.

In order for the measurement information obtained to be used, it has to be retrieved from the sensing device. Because of the size and accessibility constraints on a sensor device implanted in the body, there are shortcomings associated with providing the sensing device with data transmission circuitry and/or a power supply. Therefore, there is a need in the art for an improved sensor device implanted in the body and system for retrieving data from the implanted sensor device.

SUMMARY OF THE INVENTION

In accordance with the present invention, an apparatus is provided for retrieving information from a sensor device, comprising an internal sensor unit for taking quantitative analyte measurements, including a first coil forming part of a power supply for said sensor unit, a load coupled to said first coil, and a sensor circuit for modifying said load in accordance with sensor measurement information obtained by said sensor circuit; an external unit including a second coil which is mutually inductively coupled to said first coil upon said second coil coming into a predetermined proximity distance from said first coil, an oscillator for driving said second coil to induce a charging current in said first coil, and a detector for detecting variations in a load on said second coil induced by changes to said load in said internal sensor unit and for providing information signals corresponding to said load changes; and a processor for receiving and processing said information signals.

BRIEF DESCRIPTION OF THE DRAWINGS

The invention will be more fully understood with reference to the following detailed description of a preferred embodiment in conjunction with the accompanying drawings, which are given by way of illustration only and thus are not limitative of the present invention, and wherein.

DETAILED DESCRIPTION OF THE PREFERRED EMBODIMENT

Figure 1:
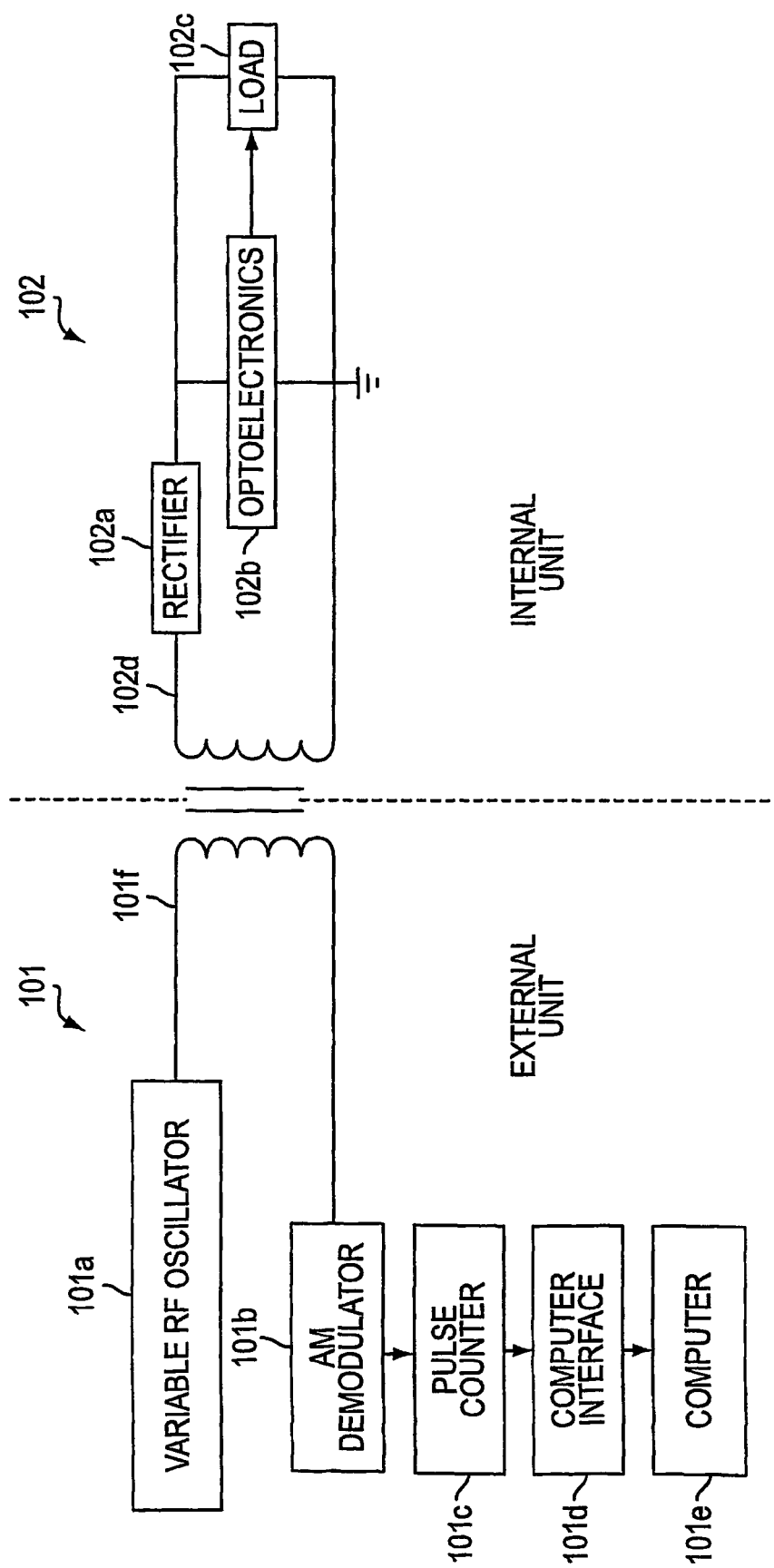
FIG. 1 is a block diagram of one preferred embodiment according to the present invention.

FIG. 1 shows a block diagram of one preferred embodiment of an implanted fluorescence sensor processing system according to the present invention.

The system includes an external unit 101 and an internal unit 102. In one example of an application of the system, the internal unit 102 would be implanted either subcutaneously or otherwise within the body of a subject. The internal unit contains optoelectronics circuitry 102b, a component of which may be comprised of a fluorescence sensing device as described more fully hereinafter with reference to FIGS. 6-8. The optoelectronics circuitry 102b obtains quantitative measurement information and modifies a load 102c as a function of the obtained information. The load 102c in turn varies the amount of current through coil 102d, which is coupled to coil 101f of the external unit. An amplitude modulation (AM) demodulator 101b detects the current variations induced in coil 101f by coil 102d coupled thereto, and applies the detected signal to processing circuitry, such as a pulse counter 101c and computer interface 101d, for processing the signal into computer-readable format for inputting to a computer 101e.

A variable RF oscillator 101a provides an RF signal to coil 101f, which in turn provides electromagnetic energy to coil 102d, when the coils 101f and 102d are within close enough proximity to each other to allow sufficient inductive coupling between the coils. The energy from the RF signal provides operating power for the internal unit 102 to obtain quantitative measurements, which are used to vary the load 102c and in turn provide a load variation to the coil 101f that is detected by the external unit and decoded into information. The load variations are coupled from the internal unit to the external unit through the mutual coupling between the coils 101f and 102d. The loading can be improved by tuning both the internal coil and the external coil to approximately the same frequency, and increasing the Q factor of the resonant circuits by appropriate construction techniques. Because of their mutual coupling, a current change in one coil induces a current in the other coil. The induced current is detected and decoded into corresponding information.

RF oscillator 101a drives coil 101f, which induces a current in coil 102d. The induced current is rectified by a rectifier circuit 102a and used to power the optoelectronics 102b. Data is generated by the optoelectronics in the form of a pulse train having a frequency varying as a function of the intensity of light emitted by a fluorescence sensor, such as described in the aforementioned '313 patent. The pulse train modulates the load 102c in a manner so as to temporarily short the rectifier output terminal to ground. This change in load causes a corresponding change in the current through the internal coil 102d, thereby causing a change in the magnetic field surrounding external coil 101f. This change in magnetic field causes a proportional change in the voltage across coil 101f, which is observable as an amplitude modulation. The following equation describes the voltage seen on the external coil:

$$V = I[Z + ((\omega M)^2)/Zs] \quad (1)$$

where
V=voltage across the external coil
I=current in the external coil
Z=impedance of the primary coil
ω=frequency (rad/sec)
M=mutual inductance between the coils
Zs=impedance of the sensor equivalent circuit As shown by equation (1), there is a direct relationship between the voltage across the external coil and the impedance presented by the internal sensor circuit. While the impedance Zs is a complex number having both a real and imaginary part, which corresponds respectively to changes in amplitude and frequency of the oscillation signal, the system according to the present embodiment deals only with the real part of the interaction. It will be recognized by those skilled in the art that both types of interaction may be detected by appropriately modifying the external circuit, to improve the signal-to-noise ratio.

Figure 2:
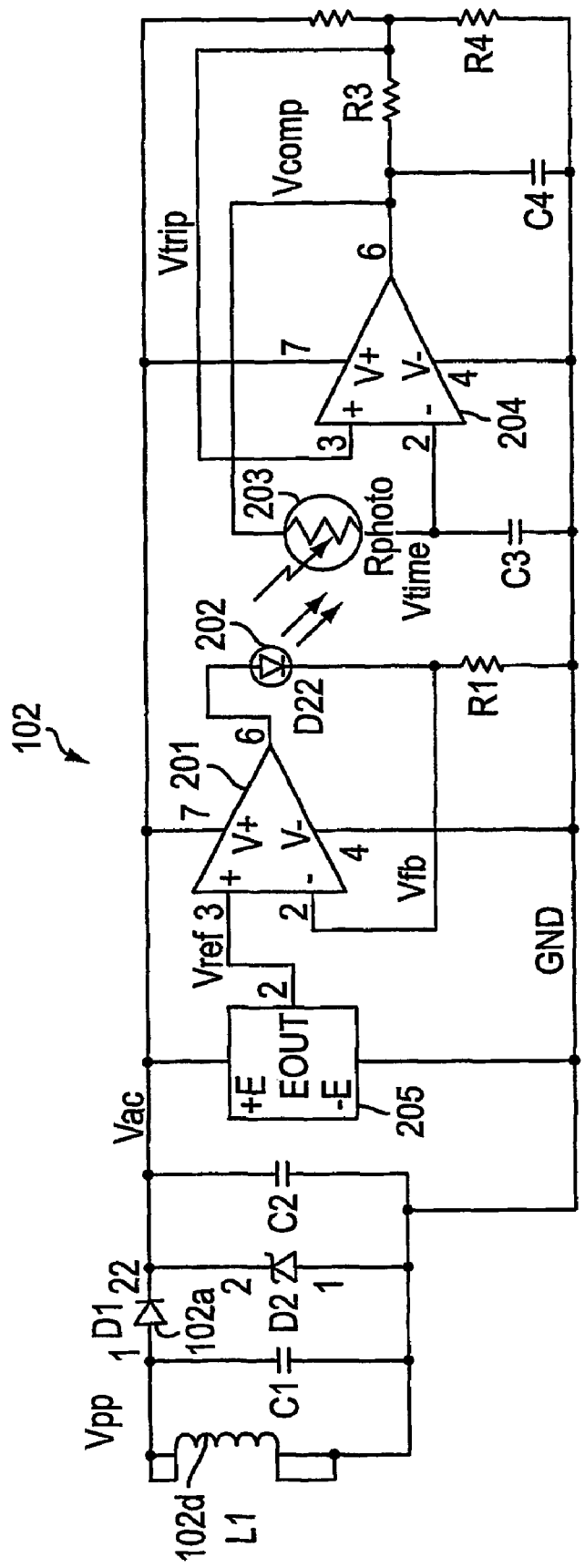
FIG. 2 is a schematic diagram of an internal sensor device unit according to one preferred embodiment of the invention.

FIG. 2 shows a schematic diagram of one embodiment of an internal sensor device unit according to the invention. The coil 102d (L1) in conjunction with capacitor C1, diode D1 (rectifier 102a) zener diode D2 and capacitor C2 constitute a power supply for the internal unit 102. Current induced in coil L1 by the RF voltage applied to external coil 101f by oscillator 101a (see FIG. 1) is resonated in the L-C tank formed by L1 and capacitor C1, rectified by diode D1, and filtered by capacitor C2. Zener diode D2 is provided to prevent the voltage being applied to the circuit from exceeding a maximum value, such as 5 volts. As is known by those skilled in the art, if the voltage across capacitor C2 starts to exceed the reverse breakdown voltage of the zener diode D2, diode D2 will start to conduct in its reverse breakdown region, preventing the capacitor C2 from becoming overcharged with respect to the maximum allowable voltage for the circuit.

Voltage regulator 205 receives the voltage from capacitor C2 and produces a fixed output voltage $V_{ref}$ to the noninverting input of operational amplifier 201. The output terminal of the operational amplifier 201 is connected to a light-emitting diode (LED) 202 connected in series with a feedback resistor R1. The inverting input terminal of operational amplifier 201 is supplied with the voltage across R1, to thereby regulate the current through LED 202 to $V_{ref}/R1$ (ignoring small bias current). Light emitted from LED 202 is incident on the sensor device (not shown) and causes the sensor device to emit light as a function of the amount of the particular analyte being monitored. The light from the sensor device impinges on the photosensitive resistor 203, whose resistance changes as a function of the amount of light incident thereon. Photoresistor 203 is connected in series with a capacitor C3, and the junction of the photoresistor and the capacitor C3 is connected to the inverting input terminal of comparator 204. The other end of photoresistor 203 is connected to the output terminal of the comparator 204 through a conductor $V_{comp}$. The output of the comparator 204 is also connected to a load capacitor C4 and a resistor network R2, R3 and R4. The comparator forms a variable resistance oscillator, with switching points determined by the values of R2, R3 and R4. C3 is a charge-up capacitor, which determines the base frequency of the oscillator for a given light level. This frequency is given by $$f = 1/(1.38 * Rphoto * C3) \quad (2)$$

$$Rphoto = R_{2fc}[10^{\gamma \log(a/2fc)}] \quad (3)$$

where
  $R_{2fc}$ (=24 kΩ) is the resistance of 203 at 2 footcandles
  γ (=0.8) is the sensitivity of the photoresistor
  a=the incident light level in footcandles Equation (3) can be inverted to determine the intensity of light for a given photoresistance; in conjunction with equation (2), the light intensity can be determined from frequency. Of course, the values given above are provided as examples only for purposes of explanation. Such values are determined on the basis of the particular photoresistor geometry and materials used.

The comparator 204 switches to a high output when Vtime=V/3, Vcomp=V, and Vtrip =2V/3. Capacitor C3 begins to charge with time constant Rphoto*Ctime. When Vtime reaches 2V/3 the comparator switches states to a low output, changing Vcomp to Vcomp=0, and Vtrip to Vtrip=V/3. At this point C3 will discharge through Rphoto. Therefore a 50% duty cycle is established, with the frequency being determined by equation (2). Rphoto varies as a function of incident light, given by equation (3).

C4 is a load capacitor, which causes a voltage across C2 to decrease when the comparator switches states. C4 must be charged from 0V to Vdc when comparator 204 switches to a high output level state. The current through C4 is supplied by C2, causing the voltage across C2 to decrease. This in turn causes current to flow through rectifier 102a to begin charging capacitor C2, changing the instantaneous load on the tank circuit including internal coil 102d. This load is reflected into the impedance of the external coil 101f as given by equation (1).

Figure 3:
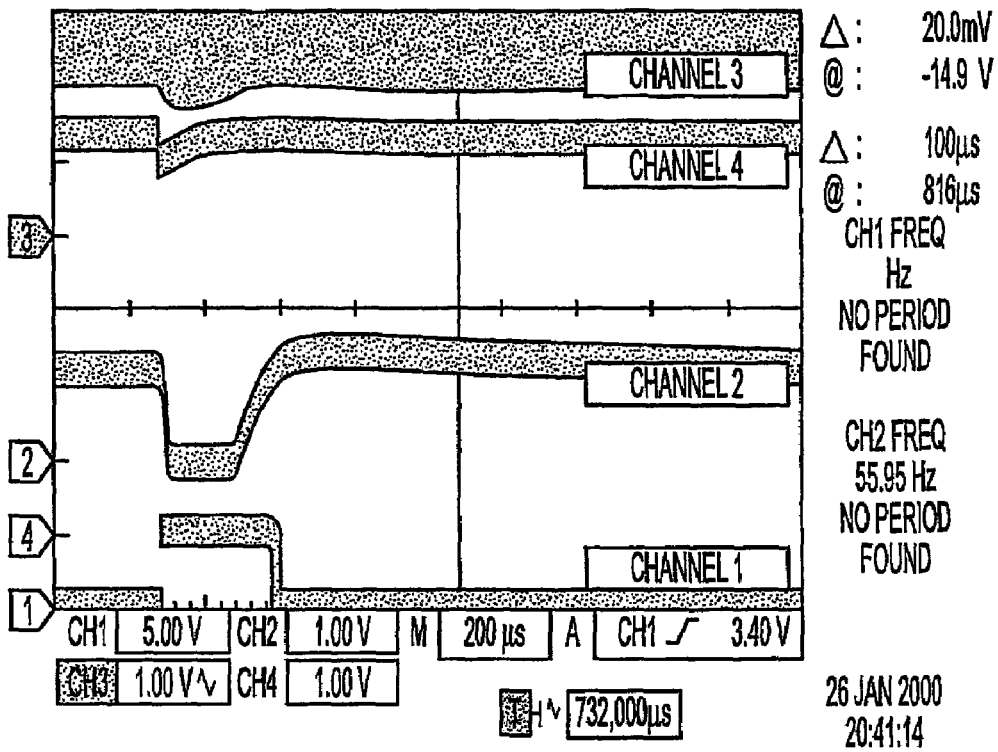
FIGS. 3 and 4 are waveform diagrams illustrating signal waveforms at various points in the sensor device circuit.
Figure 4:
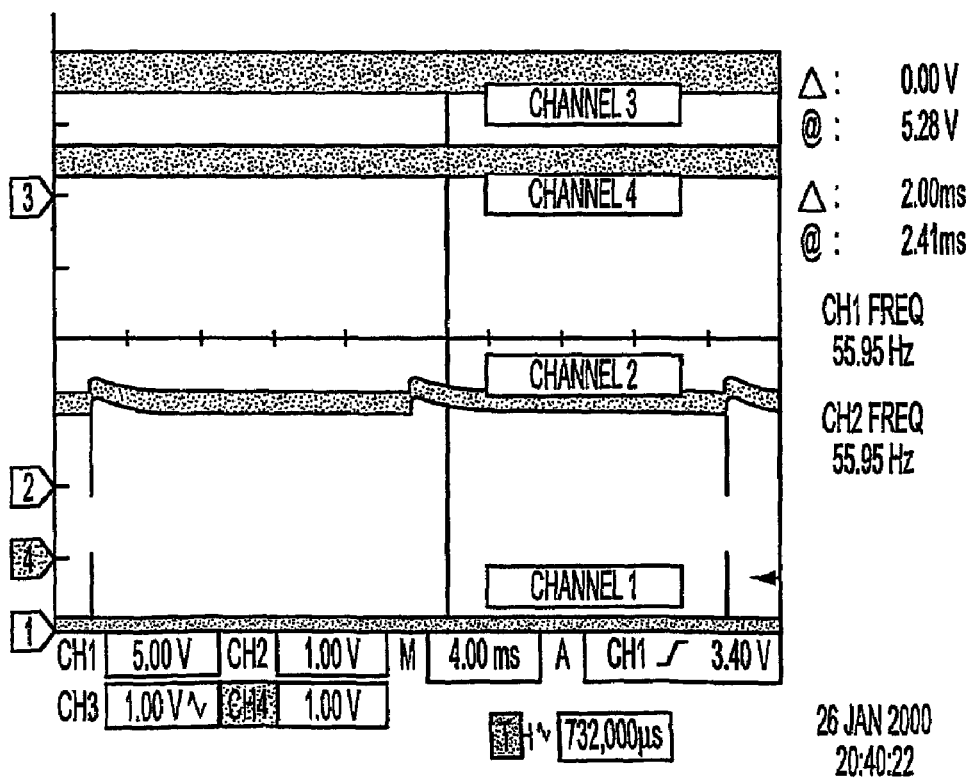

The sensor operation for a single pulse is illustrated in FIG. 3. Channel 4 is the DC voltage on C2, channel 3 shows the same pulse on the external coil 101f, and the output of the AM demodulator is shown at channel 2. Channel 1 shows the output of a comparator which converts the AM demodulator output to a square wave capable of being processed by a digital counter. FIG. 4 shows two complete operation cycles, with the same channel designations indicating the same points in the circuit.

Figure 5A:
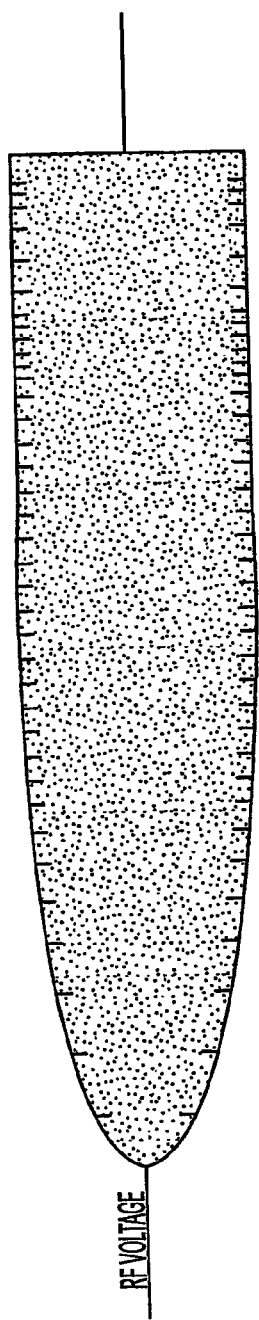
FIGS. 5A-5e are diagrams of signals produced by the external data receiving unit.
Figure 5B:
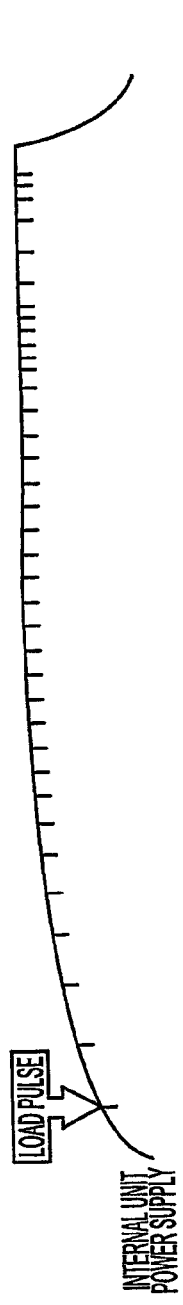
Figure 5C:
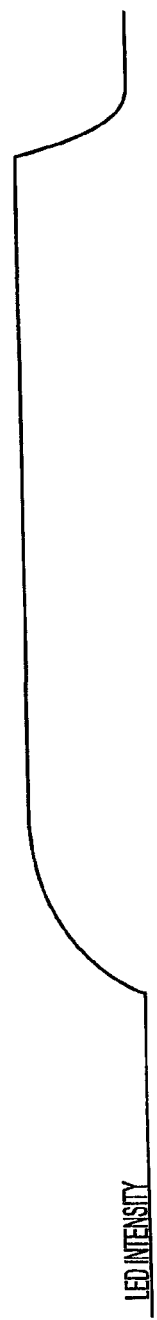
Figure 5D:
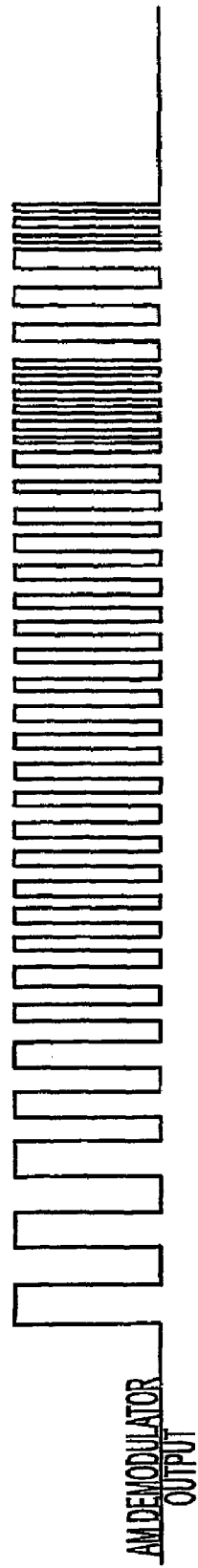
Figure 5E:
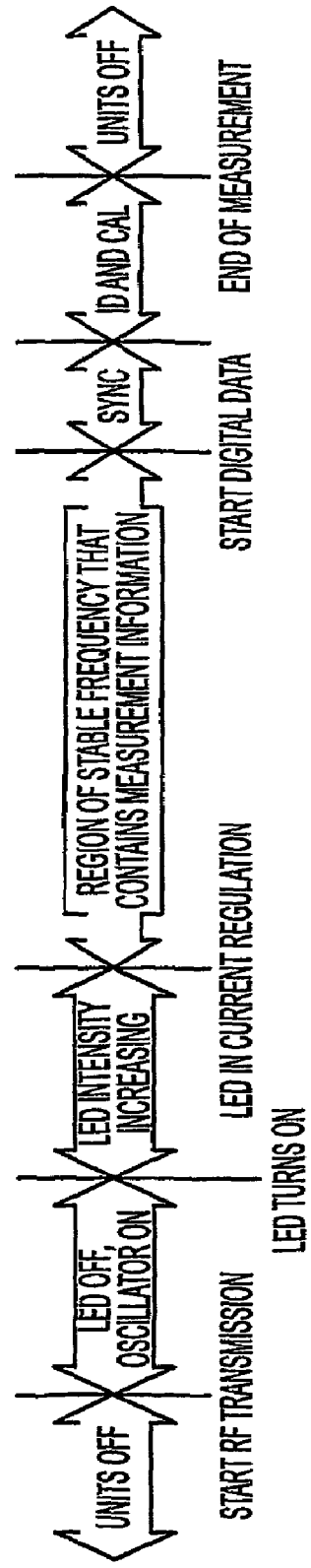

The external unit 101 uses a microprocessor to implement the pulse counter 101c. When sufficient data has been received to obtain a valid reading, the processor shuts down the RF oscillator. FIGS. 5A-5E illustrate timing diagrams for a measurement reading. FIG. 5A shows the envelope of the RF voltage signal applied to the external coil; FIG. 5B shows the waveform of the internal power supply voltage; FIG. 5C shows a waveform of the intensity of LED 202; FIG. 5D shows the output of the AM demodulator 101b; and FIG. 5E shows the timing of the state of circuit operations in accordance with the power supplied to the sensor unit. The internal unit power supply ramps up as the field strength increases. When the power supply output crosses the threshold voltage of the LED plus the feedback voltage, the LED turns on. The AM demodulator output contains the measurement data and digital data in the form of ID codes and other parameters specific to the subject in which the internal unit is implanted. This data is encoded on the RF voltage signal through time division multiplexing of the optoelectronic output with digital identification and parameter storage circuits (not shown). The digital circuits use the RF voltage to generate appropriate clock signals.

The internal storage circuits can store ID codes and parametric values such as calibration constants. This information is returned along with each reading or quantitative measurement. The signals are clocked out by switching from analog pulse train loading to digitally controlled loading at a predefined point in the measurement sequence. This point is detected in the external unit by detecting a predefined bit synchronization pattern in the output data stream. The ID number is used to identify a particular subject and to prevent data corruption when two or more subjects are in the vicinity of the external unit. The calibration factors are applied to the measurement information to obtain analyte levels in clinical units.

Figure 6:
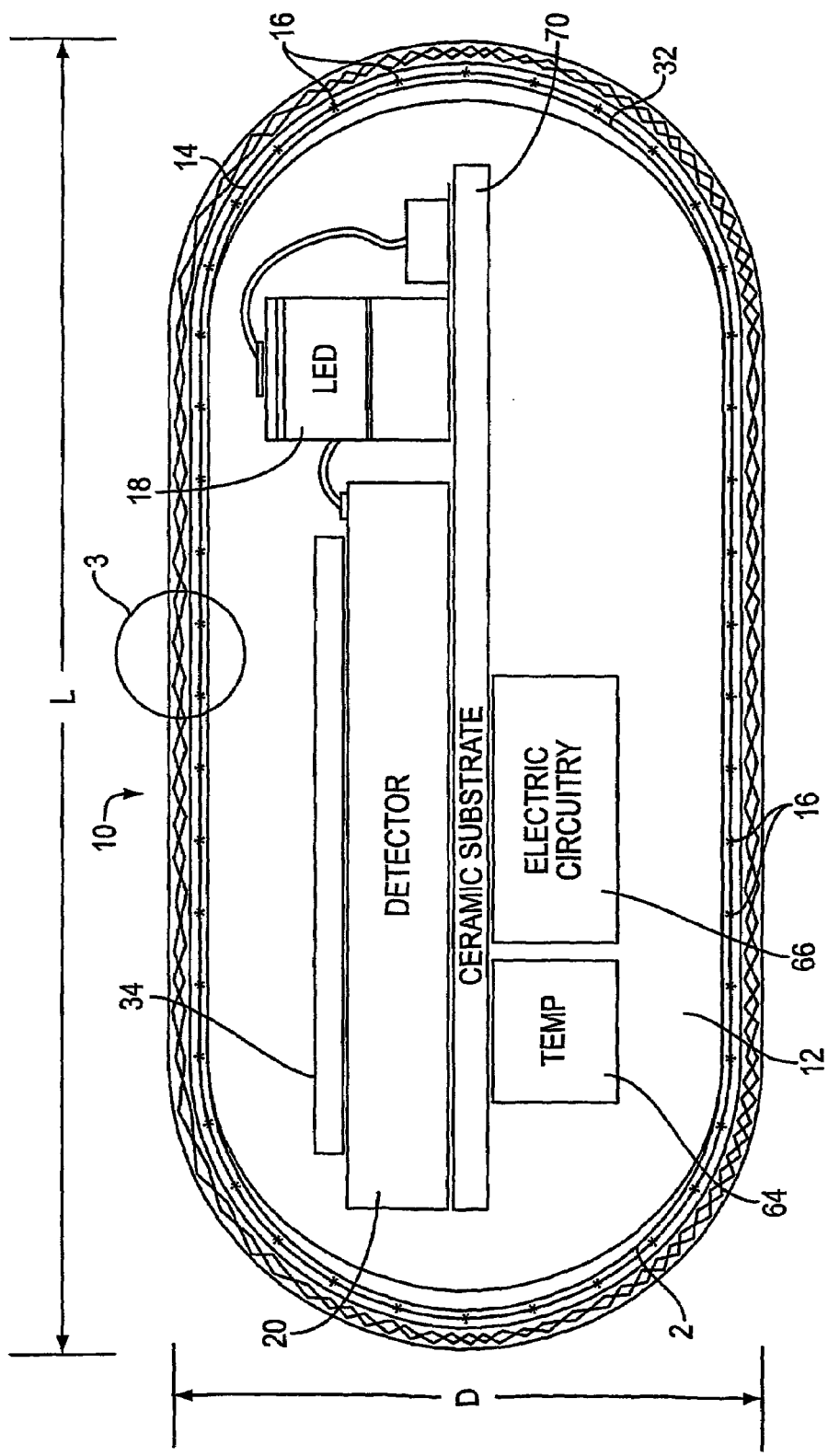
FIG. 6 is a schematic, section view of an implantable fluorescence-based sensor according to the invention.

A sensor 10 according to one aspect of the invention, which operates based on the fluorescence of fluorescent indicator molecules, is shown in FIG. 6. The sensor 10 is composed of a sensor body 12; a matrix layer 14 coated over the exterior surface of the sensor body 12, with fluorescent indicator molecules 16 distributed throughout the layer; a radiation source 18, e.g. an LED, that emits radiation, including radiation over a wavelength or range of wavelengths which interact with the indicator molecules, i.e., in the case of a fluorescence-based sensor, a wavelength or range of wavelengths which cause the indicator molecules 16 to fluoresce; and a photosensitive element 20, e.g. a photodetector, which, in the case of a fluorescence-based sensor, is sensitive to fluorescent light emitted by the indicator molecules 16 such that a signal is generated in response thereto that is indicative of the level of fluorescence of the indicator molecules. The sensor 10 further includes a module or housing 66 containing electronic circuitry, and a temperature sensor 64 for providing a temperature reading. In the simplest embodiments, indicator molecules 16 could simply be coated on the surface of the sensor body. In preferred embodiments, however, the indicator molecules are contained within the matrix layer 14, which comprises a biocompatible polymer matrix that is prepared according to methods known in the art and coated on the surface of the sensor body. Suitable biocompatible matrix materials, which must be permeable to the analyte, include methacrylates and hydrogels which advantageously can be made selectively permeable to the analyte.

The sensor body 12 advantageously is formed from a suitable, optically transmissive polymer material which has a refractive index sufficiently different from that of the medium in which the sensor will be used such that the polymer will act as an optical wave guide. Preferred materials are acrylic polymers such as polymethylmethacrylate, polyhydroxypropylmethacrylate and the like, and polycarbonates such as those sold under the trademark Lexan®. The material allows radiation generated by the radiation source 18 (e.g., light at an appropriate wavelength in embodiments in which the radiation source is an LED) and, in the case of a fluorescence-based embodiment, fluorescent light emitted by the indicator molecules, to travel through it Radiation source or LED 18 corresponds to LED 202 shown in FIG. 2.

Figure 7:
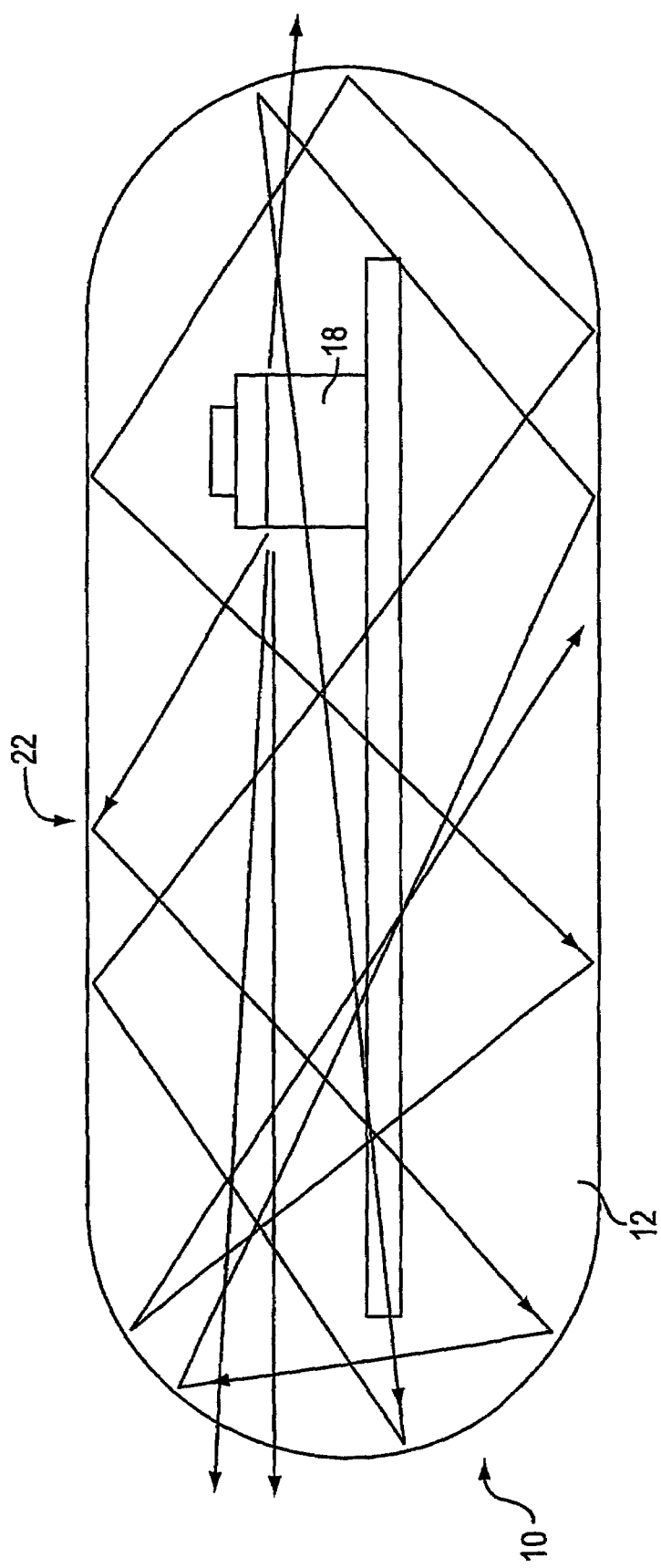
FIG. 7 is a schematic diagram of the fluorescence-based sensor shown in FIG. 6 illustrating the wave guide properties of the sensor.

As shown in FIG. 7, radiation (e.g., light) is emitted by the radiation source 18 and at least some of this radiation is reflected internally at the surface of the sensor body 12, e.g., as at location 22, thereby "bouncing" back-and-forth throughout the interior of the sensor body 12.

It has been found that light reflected from the interface of the sensor body and the surrounding medium is capable of interacting with indicator molecules coated on the surface (whether coated directly thereon or contained within a matrix), e.g., exciting fluorescence in fluorescent indicator molecules coated on the surface. In addition, light which strikes the interface at angles (measured relative to a direction normal to the interface) too small to be reflected passes through the interface and also excites fluorescence in fluorescent indicator molecules. Other modes of interaction between the light (or other radiation) and the interface and the indicator molecules have also been found to be useful depending on the construction of and application for the sensor. Such other modes include evanescent excitation and surface plasma resonance type excitation.

Figure 8:
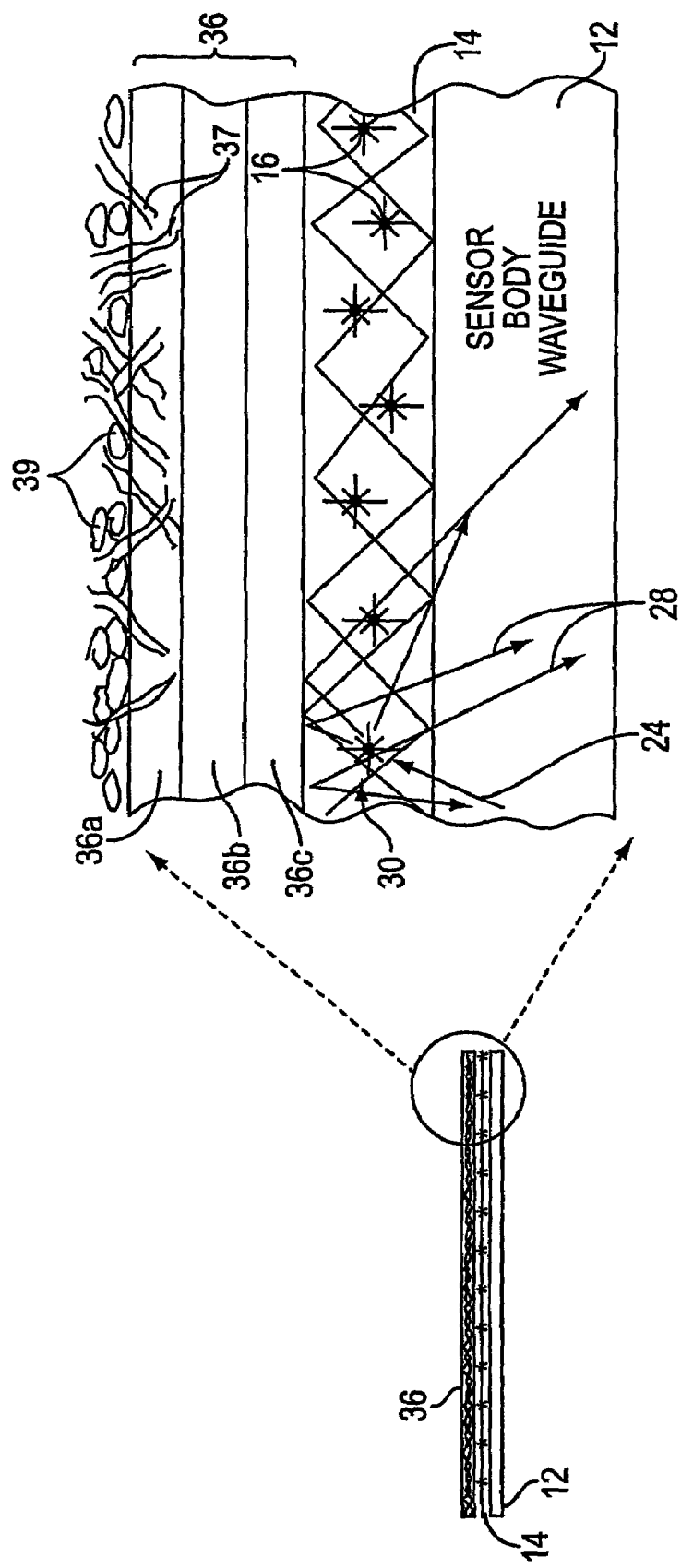
FIG. 8 is a detailed view of the circled portion of FIG. 6 demonstrating internal reflection within the body of the sensor and a preferred construction of the sensor/tissue interface layer.

As demonstrated by FIG. 8, at least some of the light emitted by the fluorescent indicator molecules 16 enters the sensor body 12, either directly or after being reflected by the outermost surface (with respect to the sensor body 12) of the matrix layer 14, as illustrated in region 30. Such fluorescent light 28 is then reflected internally throughout the sensor body 12, much like the radiation emitted by the radiation source 18 is, and, like the radiation emitted by the radiation source, some will strike the interface between the sensor body and the surrounding medium at angles too small to be reflected and will pass back out of the sensor body.

As filter illustrated in FIG. 6, the sensor 10 may also include reflective coatings 32 formed on the ends of the sensor body 12, between the exterior surface of the sensor body and the matrix layer 14, to maximize or enhance the internal reflection of the radiation and/or light emitted by fluorescent indicator molecules. The reflective coatings may be formed, for example, from paint or from a metallized material.

An optical filter 34 preferably is provided on the light-sensitive surface of the photodetector 20, which is manufactured of a photosensitive material. Photodetector 20 corresponds to photodetector 203 shown in FIG. 2. Filter 34, as is known from the prior art, prevents or substantially reduces the amount of radiation generated by the source 18 from impinging on the photosensitive surface of the photosensitive element 20. At the same time, the filter allows fluorescent light emitted by fluorescent indicator molecules to pass through it to strike the photosensitive region of the detector. This significantly reduces "noise" in the photodetector signal that is attributable to incident radiation from the source 18.

The application for which the sensor 10 according to one aspect of the invention was developed in particular—although by no means the only application for which it is suitable—is measuring various biological analytes in the human body, e.g., glucose, oxygen, toxins, pharmaceuticals or other drugs, hormones, and other metabolic analytes. The specific composition of the matrix layer 14 and the indicator molecules 16 may vary depending on the particular analyte the sensor is to be used to detect and/or where the sensor is to be used to detect the analyte (i.e., in the blood or in subcutaneous tissues). Two constant requirements, however, are that the matrix layer 14 facilitate exposure of the indicator molecules to the analyte and that the optical characteristics of the indicator molecules (e.g., the level of fluorescence of fluorescent indicator molecules) are a function of the concentration of the specific analyte to which the indicator molecules are exposed.

To facilitate use in-situ in the human body, the sensor 10 is formed, preferably, in a smooth, oblong or rounded shape. Advantageously, it has the approximate size and shape of a bean or a pharmaceutical gelatin capsule, i.e., it is on the order of approximately 300-500 microns to approximately 0.5 inch in length L and on the order of approximately 300 microns to approximately 0.3 inch in depth D, with generally smooth, rounded surfaces throughout. The device of course could be larger or smaller depending on the materials used and upon the intended uses of the device. This configuration permits the sensor 10 to be implanted into the human body, i.e., dermally or into underlying tissues (including into organs or blood vessels) without the sensor interfering with essential bodily functions or causing excessive pain or discomfort.

Moreover, it will be appreciated that any implant placed within the human (or any other animal's) body—even an implant that is comprised of "biocompatible" materials—will cause, to some extent, a "foreign body response" within the organism into which the implant is inserted, simply by virtue of the fact that the implant presents a stimulus. In the case of a sensor 10 that is implanted within the human body, the "foreign body response" is most often fibrotic encapsulation, i.e., the formation of scar tissue. Glucose—a primary analyte which sensors according to the invention are expected to be used to detect—may have its rate of diffusion or transport hindered by such fibrotic encapsulation. Even molecular oxygen ($O_2$), which is very small, may have its rate of diffusion or transport hindered by such fibrotic encapsulation as well. This is simply because the cells forming the fibrotic encapsulation (scar tissue) can be quite dense in nature or have metabolic characteristics different from that of normal tissue.

To overcome this potential hindrance to or delay in exposing the indicator molecules to biological analytes, two primary approaches are contemplated. According to one approach, which is perhaps the simplest approach, a sensor/tissue interface layer—overlying the surface of the sensor body 12 and/or the indicator molecules themselves when the indicator molecules are immobilized directly on the surface of the sensor body, or overlying the surface of the matrix layer 14 when the indicator molecules are contained therein—is prepared from a material which causes little or acceptable levels of fibrotic encapsulation to form. Two examples of such materials described in the literature as having this characteristic are PrecludeTM Periocardial Membrane, available from W. L. Gore, and polyisobutylene covalently combined with hydrophiles as described in Kennedy, "Tailoring Polymers for Biological Uses," Chemtech, February 1994, pp. 24-31.

Alternatively, a sensor/tissue interface layer that is composed of several layers of specialized biocompatible materials can be provided over the sensor. As shown in FIG. 8, for example, the sensor/tissue interface layer 36 may include three sublayers 36a, 36b, and 36c. The sublayer 36a, a layer which promotes tissue ingrowth, preferably is made from a biocompatible material that permits the penetration of capillaries 37 into it, even as fibrotic cells 39 (scar tissue) accumulate on it. Gore-Tex® Vascular Graft material (ePTFE), Dacron® (PET) Vascular Graft materials which have been in use for many years, and MEDPOR Biomaterial produced from high-density polyethylene (available from POREX Surgical Inc.) are examples of materials whose basic composition, pore size, and pore architecture promote tissue and vascular ingrowth into the tissue ingrowth layer.

The sublayer 36b, on the other hand, preferably is a biocompatible layer with a pore size (less than 5 micrometers) that is significantly smaller than the pore size of the tissue ingrowth sublayer 36a so as to prevent tissue ingrowth. A presently preferred material from which the sublayer 36b is to be made is the Preclude Periocardial Membrane (formerly called GORE-TEX Surgical Membrane), available from W. L. Gore, Inc., which consists of expanded polytetrafluoroethylene (ePTFE).

The third sublayer 36c acts as a molecular sieve, i.e., it provides a molecular weight cut-off function, excluding molecules such as immunoglobulins, proteins, and glycoproteins while allowing the analyte or analytes of interest to pass through it to the indicator molecules (either coated directly on the sensor body 12 or immobilized within a matrix layer 14). Many well known cellulose-type membranes, e.g., of the sort used in kidney dialysis filtration cartridges, may be used for the molecular weight cut-off layer 36c.

As will be recognized, the sensor as shown in FIG. 6 is wholly self-contained such that no electrical leads extend into or out of the sensor body, either to supply power to the sensor (e.g., for driving the source 18) or to transmit signals from the sensor. All of the electronics illustrated in FIG. 2 may be housed in a module 66 as shown in FIG. 6.

Figure 9:
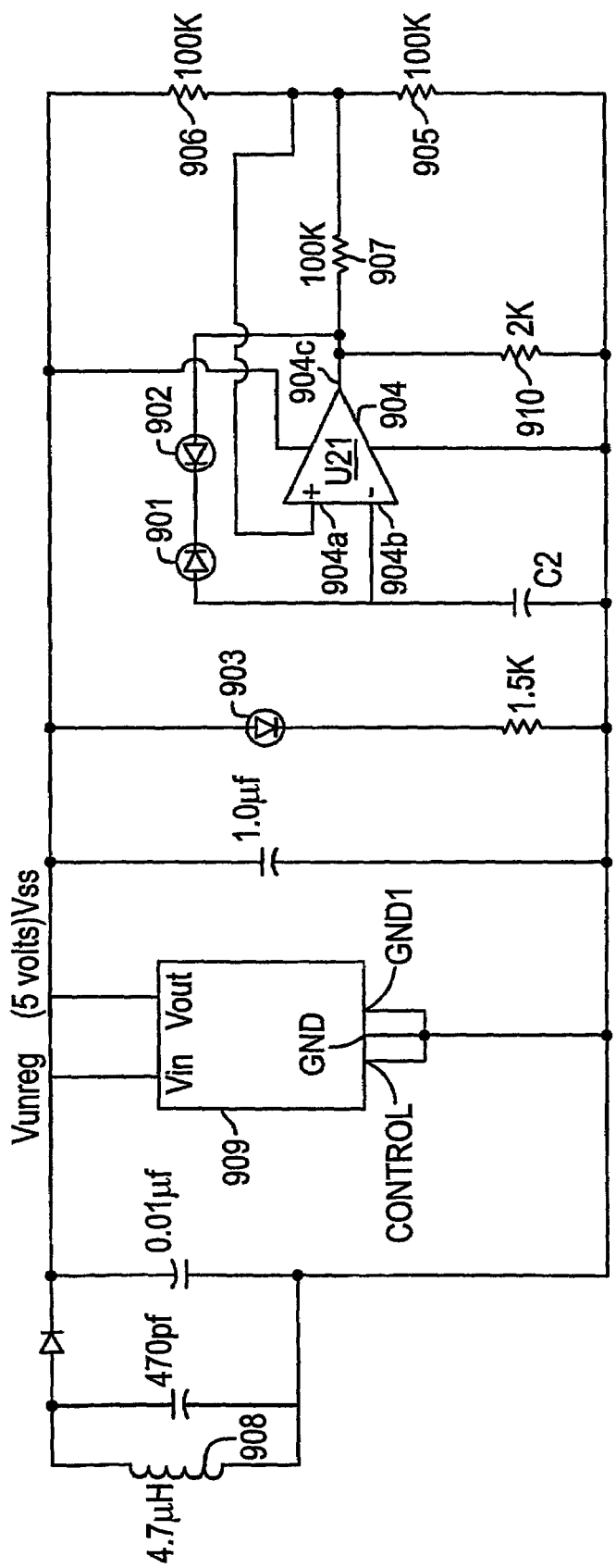
FIG. 9 is a schematic diagram of an internal sensor device unit according to a second preferred embodiment of the invention.

A second preferred embodiment of the invention is shown in FIG. 9, in which two detectors are employed, a signal channel detector 901 and a reference channel detector 902. In the first embodiment as shown in FIG. 2, a single detector 203 is used to detect radiation from the fluorescent indicator sensor device. While this system works well, it is possible that various disturbances to the system will occur that may affect the accuracy of the sensor output as originally calibrated.

Examples of such disturbances include: changes or drift in the component operation intrinsic to the sensor make-up; environmental conditions external to the sensor; or combinations thereof. Internal variables may be introduced by, among other things: aging of the sensor's radiation source; changes affecting the performance or sensitivity of the photosensitive element; deterioration of the indicator molecules; changes in the radiation transmissivity of the sensor body, of the indicator matrix layer, etc.; and changes in other sensor components; etc. In other examples, the optical reference channel could also be used to compensate or correct for environmental factors (e.g., factors external to the sensor) which could affect the optical characteristics or apparent optical characteristics of the indicator molecule irrespective of the presence or concentration of the analyte. In this regard, exemplary external factors could include, among other things: the temperature level; the pH level; the ambient light present; the reflectivity or the turbidity of the medium that the sensor is applied in; etc. The optical reference channel can be used to compensate for such variations in the operating conditions of the sensor. The reference channel is identical to the signal channel in all respects except that the reference channel is not responsive to the analyte being measured.

Use of reference channels in optical measurement is generally known in the art For example, U.S. Pat. No. 3,612,866, the entire disclosure of which is incorporated herein by reference, describes a fluorescent oxygen sensor having a reference channel containing the same indicator chemistry as the measuring channel, except that the reference channel is coated with varnish to render it impermeable to oxygen.

U.S. Pat. Nos. 4,861,727 and 5,190,729, the entire disclosures of which are incorporated herein by reference, describe oxygen sensors employing two different lanthanide-based indicator chemistries that emit at two different wavelengths, a terbium-based indicator being quenched by oxygen and a europium-based indicator being largely unaffected by oxygen. U.S. Pat. No. 5,094,959, the entire disclosure of which is also incorporated herein by reference, describes an oxygen sensor in which a single indicator molecule is irradiated at a certain wavelength and the fluorescence emitted by the molecule is measured over two different emission spectra having two different sensitivities to oxygen. Specifically, the emission spectra which is less sensitive to oxygen is used as a reference to ratio the two emission intensities. U.S. Pat. Nos. 5,462,880 and 5,728,422, the entire disclosures of which are also incorporated herein by reference, describe a ratiometric fluorescence oxygen sensing method employing a reference molecule that is substantially unaffected by oxygen and has a photodecomposition rate similar to the indicator molecule. Additionally, Muller, B., et al., ANALYST, Vol. 121, pp. 339-343 March 1996), the entire disclosure of which is incorporated herein by reference, describes a fluorescence sensor for dissolved $CO_2$, in which a blue LED light source is directed through a fiber optic coupler to an indicator channel and to a separate reference photodetector which detects changes in the LED light intensity.

In addition, U.S. Pat. No. 4,580,059, the entire disclosure of which is incorporated herein by reference, describes a fluorescent-based sensor containing a reference light measuring cell for measuring changes in the intensity of the excitation light source—see, e.g., column 10, lines 1, et seq.

As shown in FIG. 9, the signal and reference channel detectors are back-to-back photodiodes 901 and 902. While photodiodes are shown, many other types of photodetectors also could be used, such as photoresistors, phototransistors, and the like. LED 903 corresponds to light source 202 in FIG. 2. In operation, comparator 904 is set to trigger at ⅓ and ⅔ of the supply voltage Vss, as biased by resistors 905, 906, and 907. The trigger voltages for comparator 904 could be modified, if desired, by changing the values of the resistors. Capacitor C2 is a timing element, the value of which is adjusted for the magnitude of the signal and reference channels. The current through each photodiode is a function of the intensity or power of incident light entering it, as represented by the equation I=RP, where I=current R=responsivity (Amp/Watt) and P=light power in watts.

In the fluorescence embodiment, the incident light power impinging upon the photodiode detectors changes with analyte concentration.

Figure 10:
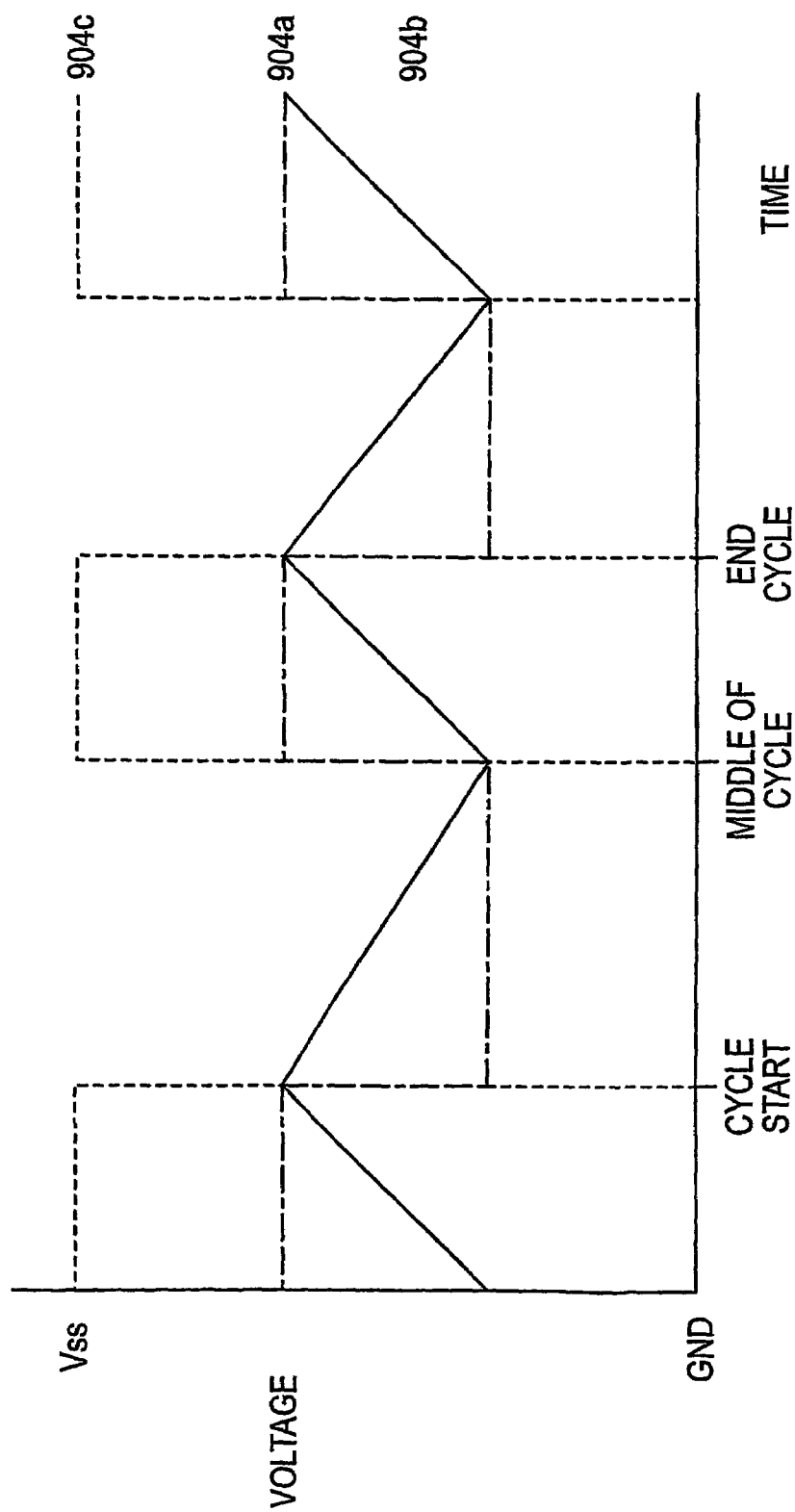
FIG. 10 is a timing diagram illustrating voltage levels of various terminals of the comparator of FIG. 9 as the detector circuit cycles through its operation.

FIG. 10 is a timing diagram showing the voltage levels of the terminals 904a, 904b, and 904c of the comparator 904. At the cycle start, the voltage level of output terminal 904c is at ground (low output state), the voltage level of capacitor C2 (which corresponds to the voltage level at input terminal 904b) is at ⅔ Vss, and the voltage level of input terminal 904a is at ⅓ Vss. In this instance, photodiode 901 is forward-biased and photodiode 902 is reverse-biased. The voltage drop across the forward-biased photodiode 901 is simply its threshold voltage, while the reverse-biased photodiode 902 exhibits a current flow proportional to the incident light impinging upon it. This current discharges the capacitor C2 at a rate of dV/dt=I902/C2, until it reaches a voltage level of ⅓ Vss as shown in FIG. 10. Inserting the above equation for photodiode current results in the equation dV/dt=RP/C2. Solving for P, P=(dV*C2)/(dt*R), where dV=difference between comparator trigger points (in the example ⅓ Vss)

C2=value of capacitor C2 in farads dt=time to charge or discharge (as measured by the external unit) and R=responsivity (in amps/watts) of the photodetector At this time, the comparator 904 switches to a high output state Vss on output terminal 904c. The trigger point (input terminal 904a) is now at ⅔ Vss, and the polarity of the photodiodes 901 and 902 is now reversed. That is, photodiode 901 is now reverse-biased and photodiode 902 is now forward-biased.

Photodiode 901 now controls the charging of capacitor C2 at a rate of dV/dt=I901/C2 until the voltage of capacitor C2 reaches ⅔ Vss. When the voltage across capacitor C2 reaches ⅔ Vss, the output of the comparator 904 again switches to the low output state. So long as the system is powered and incident light is present on the photodiodes, the cycle will continue to repeat as shown in FIG. 10.

If the incident light intensity on each photodiode detector 901 and 902 is equal, then the comparator output will be a 50% duty cycle. If the incident light on each photodiode detector is not equal, then the capacitor charge current will be different than the capacitor discharge current. This is the case shown in FIG. 10, wherein the capacitor charge current is higher than the capacitor discharge current. Because the same capacitor is charged and discharged, the different charge and discharge times are a function only of the difference between the incident light levels on the two photodiode detectors. Consequently, the duty cycle of the squarewave produced by the comparator 904 is indicative of changes between incident light on the signal channel photodiode and incident light on the reference channel photodiode. Suitable algorithms for taking into account changes in duty cycle of the squarewave from the comparator in determining analyte concentration are generally known in the art (see prior art references discussed supra) and will not be further discussed herein.

Once the squarewave is established, it must be transferred to the external unit. This is done by loading the internal coil 908, and then detecting the change in load on the external coil inductively coupled to the internal coil. The loading is provided by resistor 910, which is connected to the output terminal 904c of the comparator 904. When the comparator is in a high output state, an additional current Vss/R910 is drawn from the voltage regulator 909. When the comparator is in a low output state, this additional current is not present. Consequently, resistor 910 acts as a load that is switched into and out of the circuit at a rate determined by the concentration of analyte and the output of the reference channel. Because the current through resistor 910 is provided by the internal tuned tank circuit including coil 908, the switching of the resistor load also switches the load on the tank including internal coil 908. The change in impedance of the tank caused by the changing load is detected by a corresponding change in load on the inductively coupled external coil, as described above. The voltage regulator 909 removes any effects caused by coil placement in the field. The LED 903 emits the excitation light for the indicator molecule sensor. Power for the LED 903 is provided by the voltage regulator. It is important to keep the intensity of the LED constant during an analyte measurement reading. Once the output of the voltage regulator is in regulation, the LED intensity will be constant. The step recovery time of the regulator is very fast, with the transition between loading states being rapid enough to permit differentiation and AC coupling in the external unit.

As also will be recognized, the fluorescence-based sensor embodiments described in FIGS. 6-8 are just examples to which the disclosed invention may be applied. The present invention may also be applied in a number of other applications such as, for example, an absorbance-based sensor or a refractive-index-based sensor as described in U.S. patent application Ser. No. 09/383,148, filed Aug. 28, 1999, incorporated herein by reference.

The invention having been thus described, it will be apparent to those skilled in the art that the same may be varied in many ways without departing from the spirit and scope of the invention. For example, while the invention has been described with reference to an analog circuit, the principles of the invention may be carried out equivalently through the use of an appropriately programmed digital signal processor. Any and all such modifications are intended to be encompassed by the following claims.

The invention claimed is:

1. Apparatus for retrieving information from a sensor device, comprising:
    an internal sensor unit for taking quantitative analyte measurements, including a first coil forming part of a power supply for said sensor unit, a load coupled to said first coil; and a sensor circuit for modifying said load in accordance with sensor measurement information obtained by said sensor circuit, said sensor circuit including a signal channel detector responsive to analyte measurement information, and a reference channel detector responsive to reference measurement information, outputs of said signal channel detector and said reference channel detector being combined in said sensor information for modifying said load, wherein said signal channel detector is configured to produce an output determinative of a positive transition time of said load modification, and said reference channel detector is configured to produce an output determinative of negative transition time of said modification;
    an external unit including a second coil which is mutually inductively coupled to said first coil upon said second coil being placed within a predetermined proximal distance from said first coil, an oscillator for driving said second coil to induce a charging current in said first coil, and a detector for detecting variations in a load on said second coil induced by changes to said load in said internal sensor unit and for providing information signals corresponding to said load changes; and
    a processor for receiving and processing said information signals.

2. Apparatus according to claim 1, wherein said signal channel detector and said reference channel detector are photodiodes.

3. Apparatus according to claim 2, wherein signal channel detector photodiode and said reference channel detector photodiode are connected in a cathode-to-cathode configuration.

4. Apparatus according to claim 1, wherein said load comprises a photodiode, a comparator and a resistor operatively coupled with each other to provide a varying load as a function of analyte concentration.

5. A sensor system, comprising:
    an internal unit, including:
    a first coil,
    a voltage regulator coupled to the first coil,
    a load coupled to the first coil and the voltage regulator,
    a sensor circuit, coupled to the voltage regulator and the load, to change the load based on sensor measurement information, wherein the sensor circuit includes:
        a signal channel detector to detect the presence or concentration of an analyte;
        a reference channel detector substantially unresponsive to the analyte; and
        a comparator, coupled to the load, having an output voltage level that changes based on the sensor measurement information provided by the signal and reference channel detectors, wherein the comparator is biased by a plurality of resistors which set the comparator to trigger at a plurality of predetermined voltage levels; and
    an external unit, including:
    a second coil,
    an oscillator, coupled to the second coil, to induce a charging current in the first coil when the second coil is inductively coupled to the first coil, and
    a detector, coupled to the second coil, to detect a change in the load when the second coil is inductively coupled to the first coil.

6. The system of claim 5, wherein the plurality of predetermined voltage levels includes a first predetermined voltage level associated with a low comparator output voltage level and a second predetermined voltage level associated with a high comparator output voltage level.

7. The system of claim 6, wherein the low comparator output voltage level changes the load to a low value, and the high comparator output voltage level changes the load to a high value.

8. The system of claim 5, wherein the sensor circuit includes a light source, and the signal and reference channel detectors are photodiodes arranged in a back-to-back manner.

9. The system of claim 8, wherein the load is a resistor and the sensor circuit includes a capacitor, coupled to the back-to-back photodiodes and the comparator, to control one of the input voltage levels to the comparator.

10. The system of claim 9, wherein the back-to-back photodiodes control the charging and discharging frequency of the capacitor.

11. The system of claim 10, wherein the output of the comparator is a square wave having a duty cycle and/or frequency that depends upon the incident light intensity on each photodiode.

12. The system of claim 11, wherein the detector includes an amplitude modulation demodulator and a pulse counter to encode the changes to the load.

* * * * *